ⓘ

US008454674B2

(12) United States Patent
Gunderson et al.

(10) Patent No.: US 8,454,674 B2
(45) Date of Patent: Jun. 4, 2013

(54) BIFURCATION CATHETER ASSEMBLY AND METHODS

(75) Inventors: Richard C. Gunderson, Maple Grove, MN (US); Richard Noddin, Elk River, MN (US); Adam P. Jennings, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/440,447

(22) Filed: Apr. 5, 2012

(65) Prior Publication Data

US 2012/0191173 A1 Jul. 26, 2012

Related U.S. Application Data

(63) Continuation of application No. 12/183,162, filed on Jul. 31, 2008, now Pat. No. 8,152,840.

(51) Int. Cl.
*A61F 2/06* (2006.01)
*A61M 29/00* (2006.01)

(52) U.S. Cl.
USPC .................................. 623/1.11; 604/101.01

(58) Field of Classification Search
USPC ............... 604/96.01–100.03, 101.01, 101.04, 604/101.05, 103.07; 606/192, 194; 623/1.11, 623/1.12, 1.35
See application file for complete search history.

(56) References Cited

U.S. PATENT DOCUMENTS

| | | | |
|---|---|---|---|
| 5,368,566 A | 11/1994 | Crocker | |
| 5,669,924 A | 9/1997 | Shaknovich | |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 7,220,275 B2 | 5/2007 | Davidson et al. | |
| 7,314,480 B2 * | 1/2008 | Eidenschink et al. | 623/1.11 |
| 7,344,557 B2 | 3/2008 | Yadin | |
| 7,655,030 B2 | 2/2010 | Williams et al. | |
| 7,871,396 B2 * | 1/2011 | Jennings et al. | 604/101.01 |
| 2004/0172121 A1 | 9/2004 | Eidenschink et al. | |
| 2004/0176837 A1 | 9/2004 | Atladottir et al. | |
| 2004/0249434 A1 | 12/2004 | Andreas et al. | |
| 2005/0015108 A1 * | 1/2005 | Williams et al. | 606/194 |
| 2005/0102019 A1 * | 5/2005 | Yadin | 623/1.11 |
| 2006/0116748 A1 | 6/2006 | Kaplan et al. | |
| 2007/0078505 A1 | 4/2007 | Dimitrov | |
| 2007/0203562 A1 * | 8/2007 | Malewicz et al. | 623/1.11 |
| 2007/0213804 A1 | 9/2007 | Kaplan et al. | |
| 2007/0270935 A1 | 11/2007 | Newhauser et al. | |
| 2008/0086191 A1 | 4/2008 | Valencia et al. | |

(Continued)

*Primary Examiner* — Gary Jackson
*Assistant Examiner* — Amy Shipley
(74) *Attorney, Agent, or Firm* — Seager, Tufte & Wickhem, LLC

(57) ABSTRACT

A catheter assembly includes a main catheter branch and a side catheter branch. The main catheter branch includes a main balloon, a side balloon and a side inflation member. The side inflation member intersects the side balloon at a location on the side balloon that is offset laterally from a central line passing from a distal most point on the side balloon to a proximal most point on the side balloon. The side balloon is configured to extend radially outward relative to the main balloon when the side balloon is inflated. The side catheter branch can be centrally aligned with the side balloon central line and be positioned laterally adjacent to the side inflation lumen.

10 Claims, 13 Drawing Sheets

U.S. PATENT DOCUMENTS

2008/0288041 A1 11/2008 Holman et al.
2009/0171430 A1 7/2009 Baim et al.
2010/0114018 A1* 5/2010 Noddin et al. ........... 604/101.01
2010/0114019 A1 5/2010 Dunn et al.

* cited by examiner

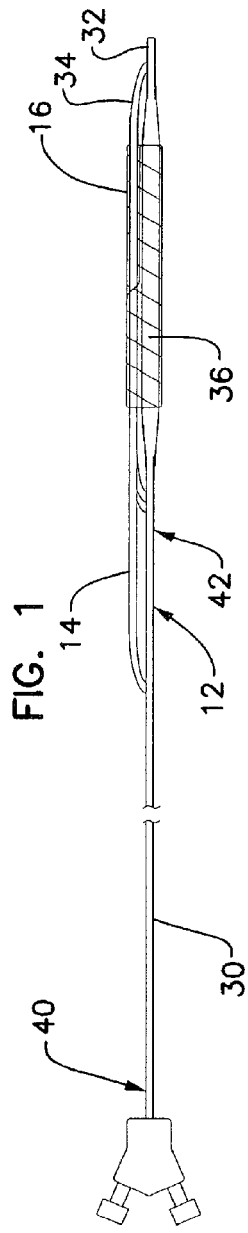
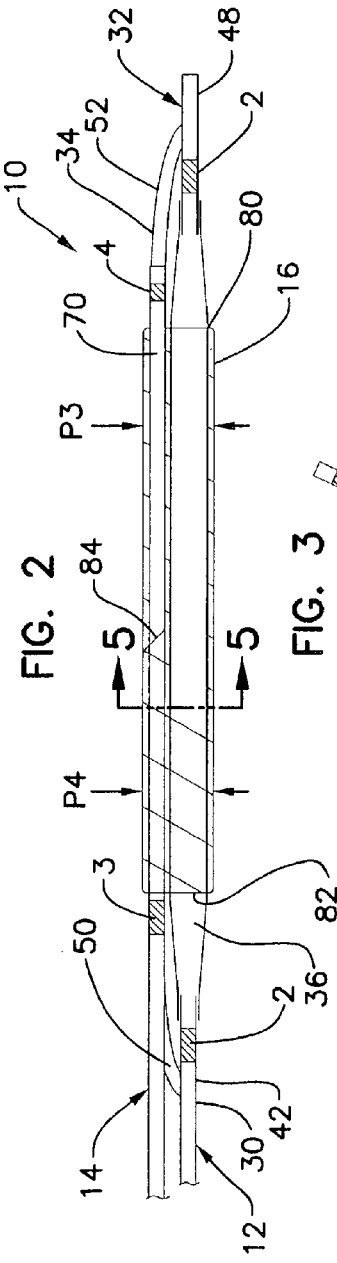
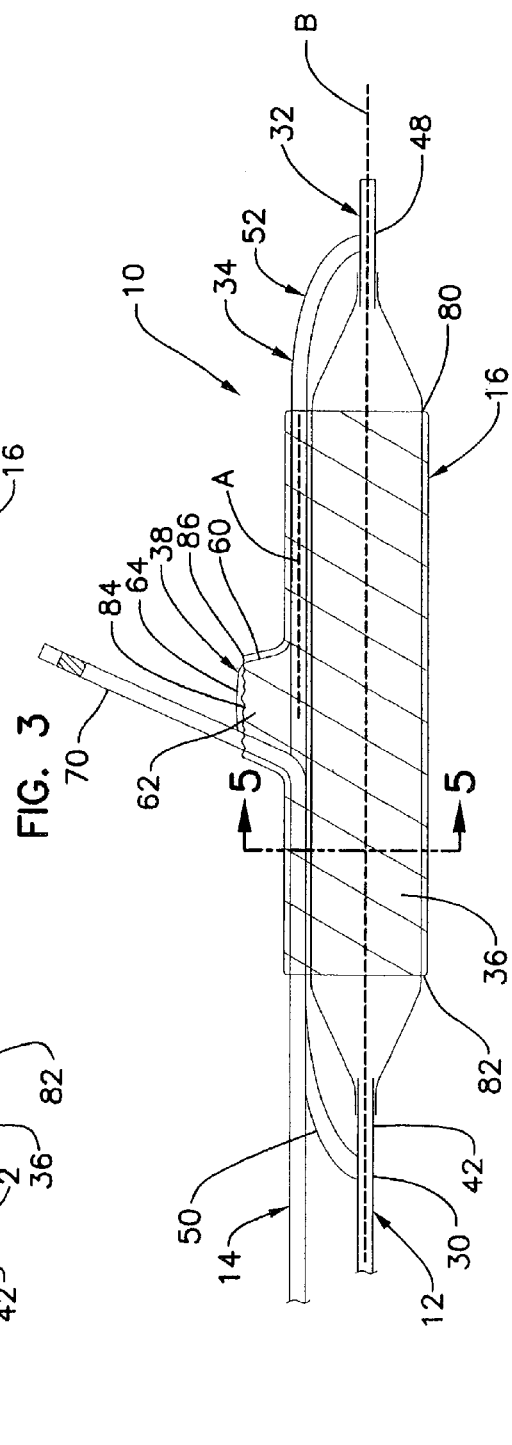

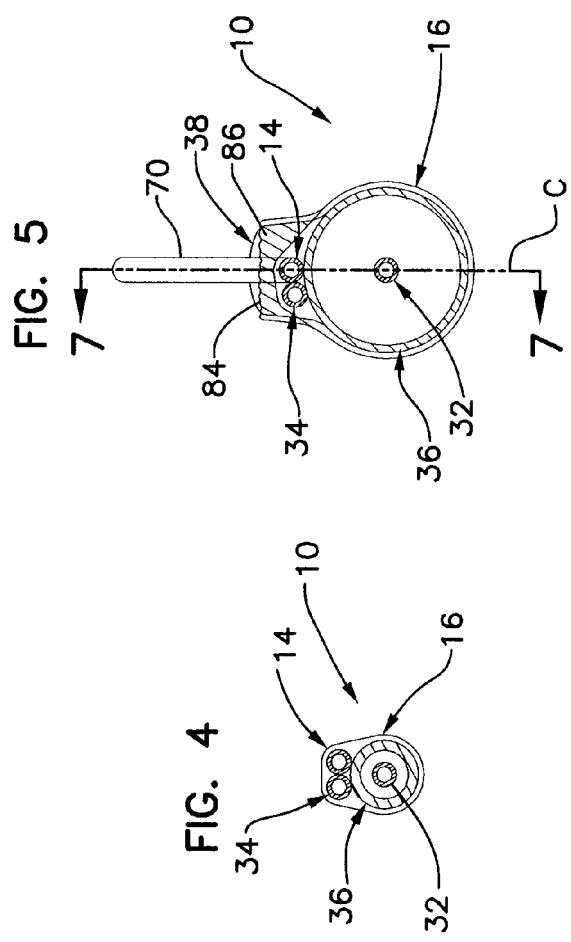
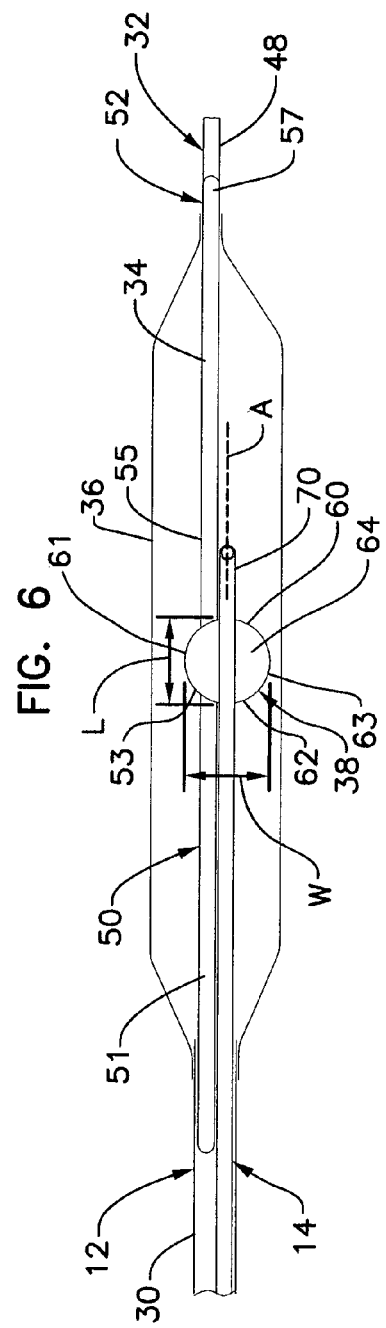

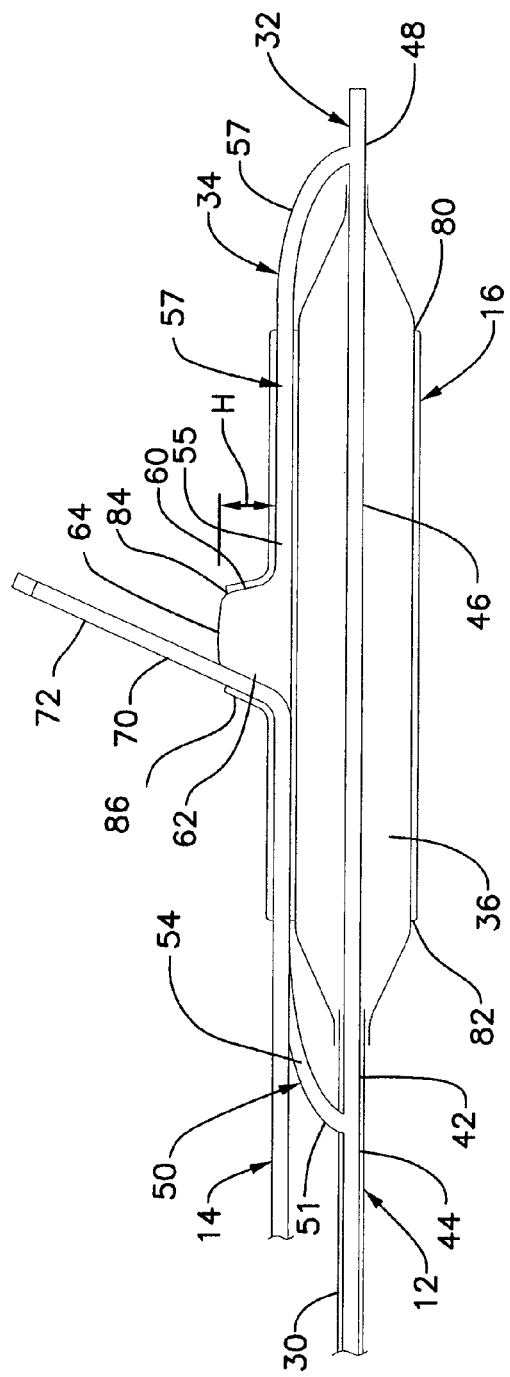

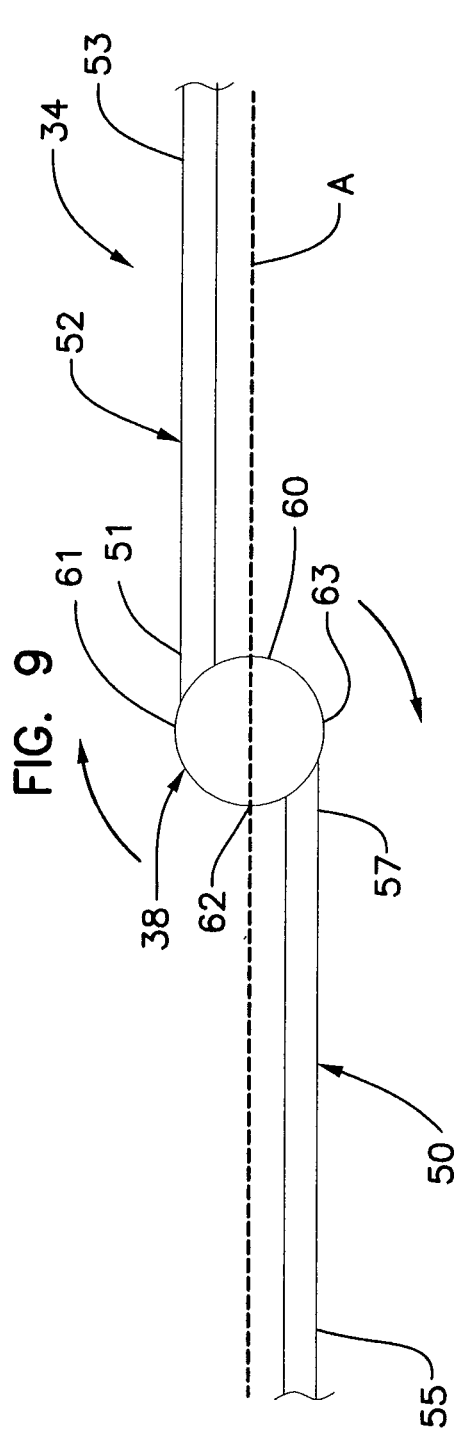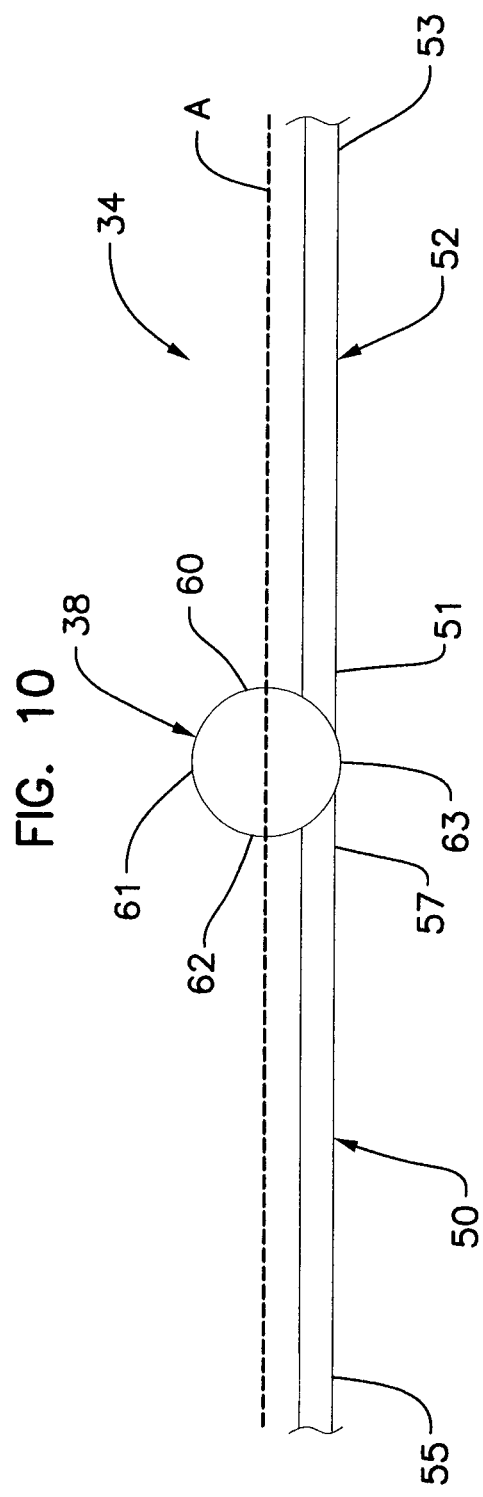

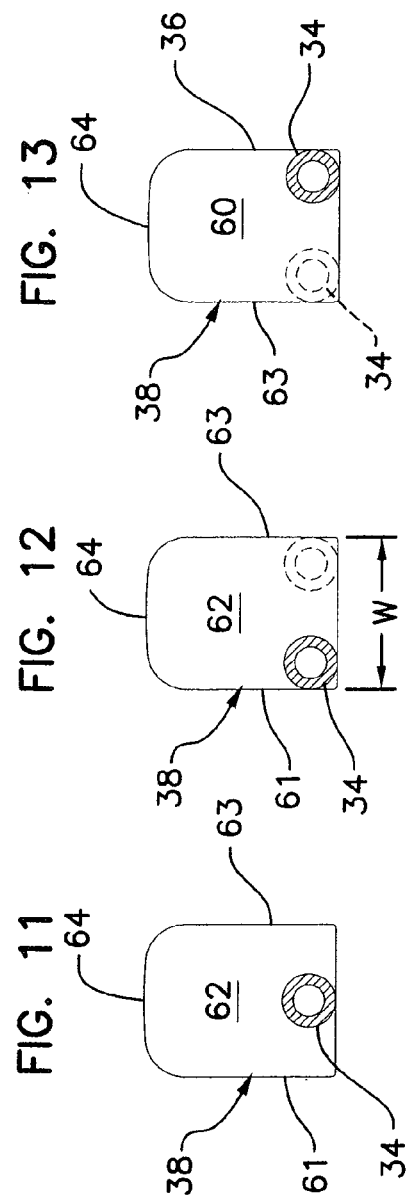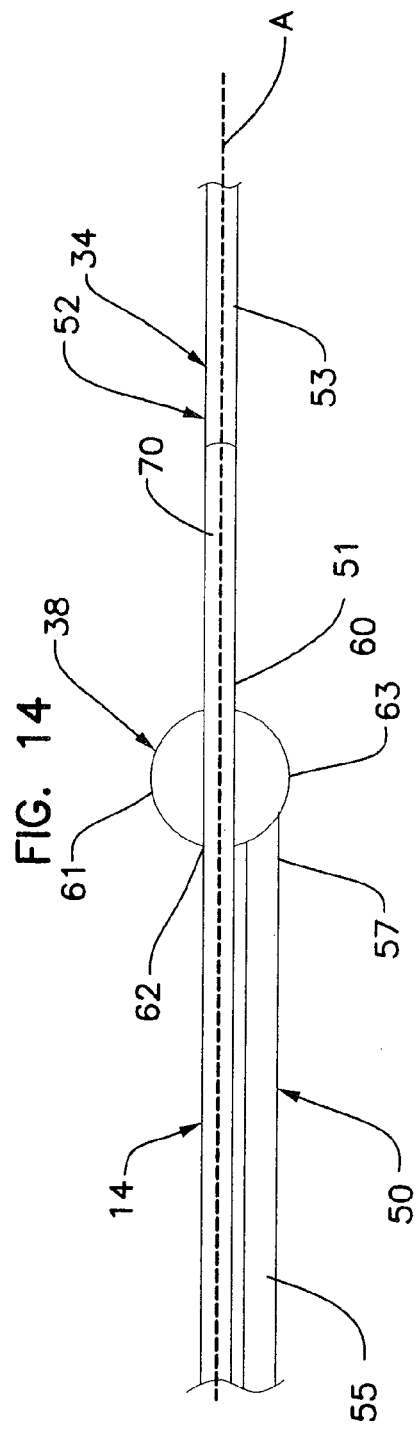

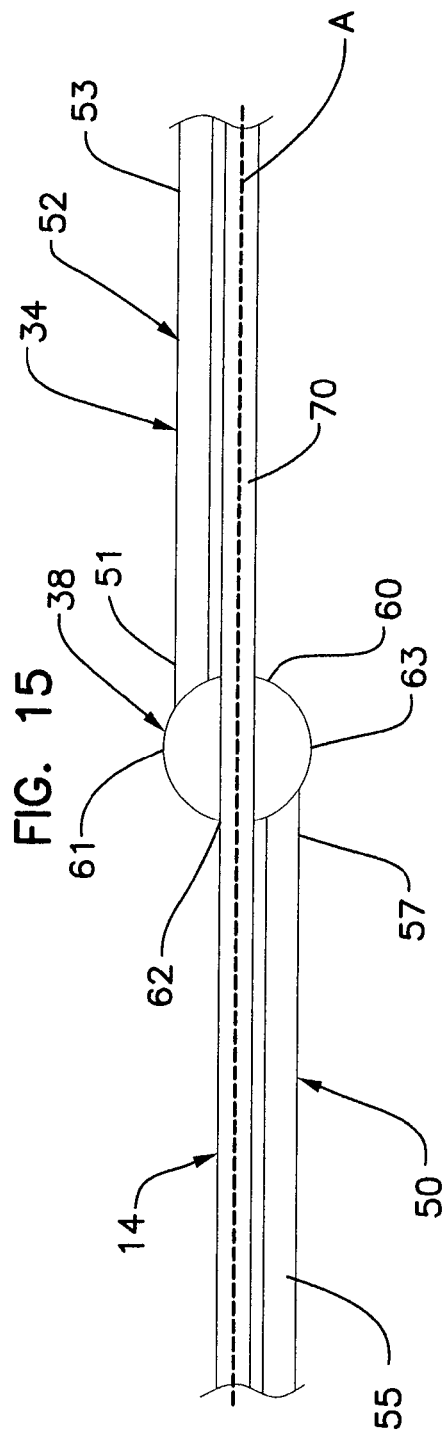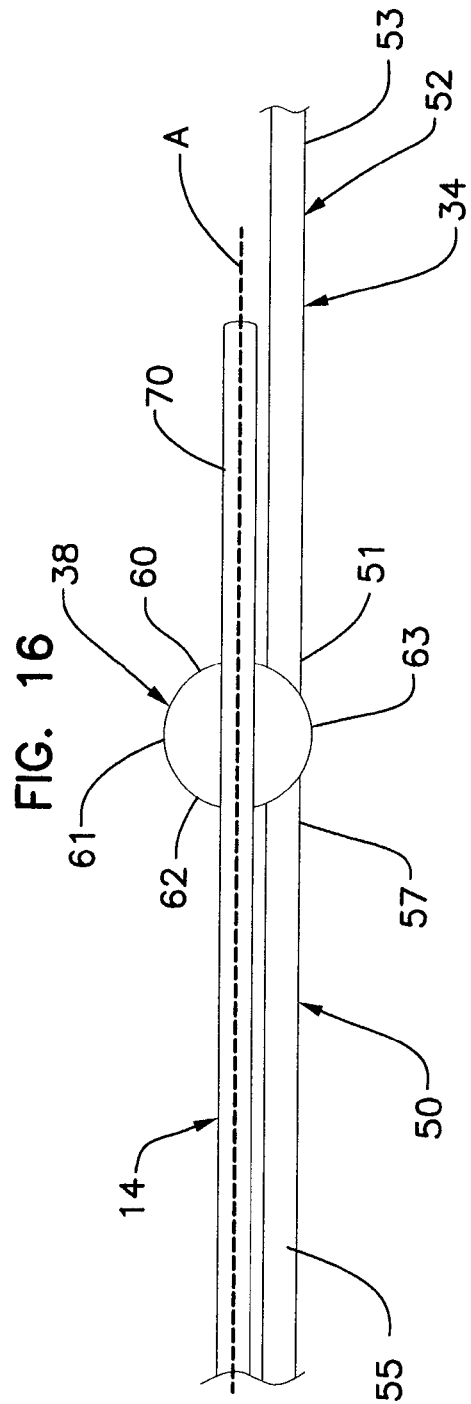

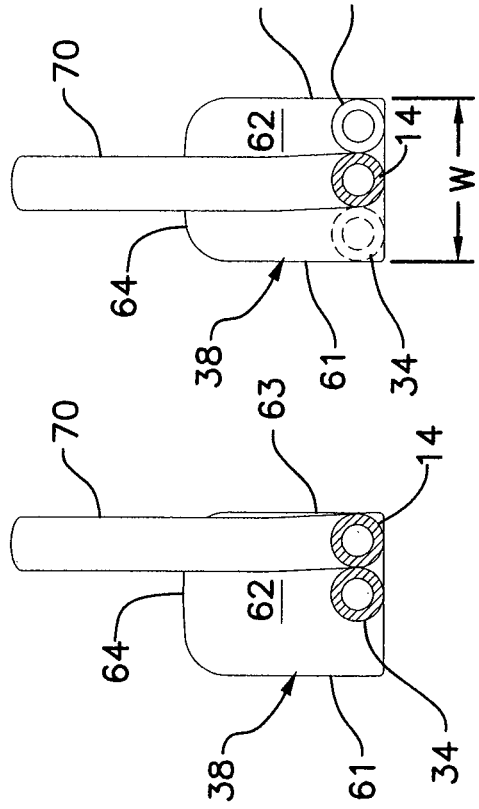

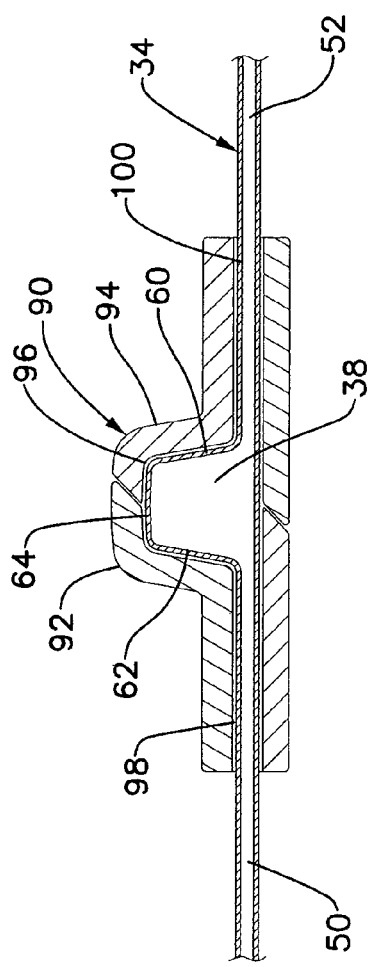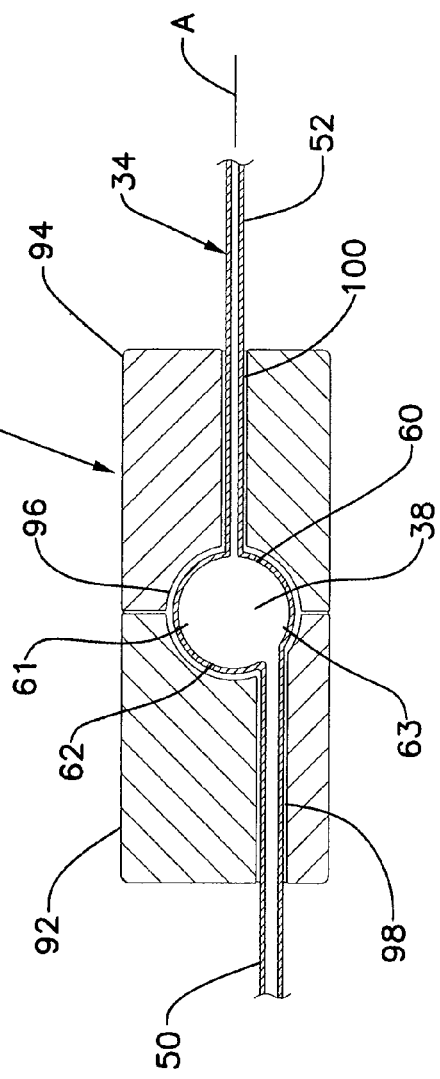

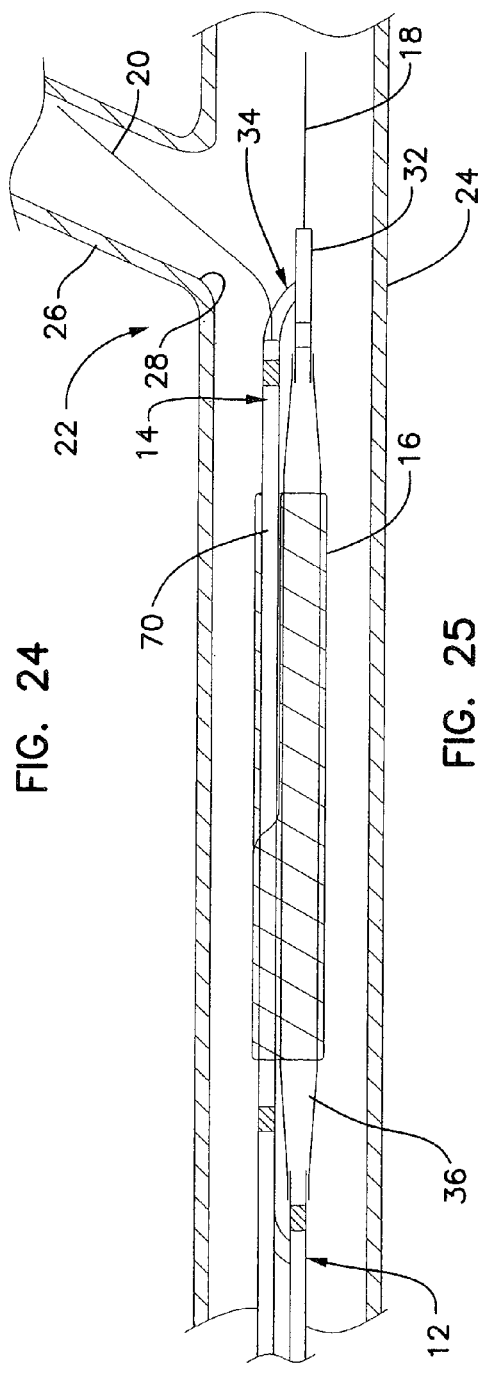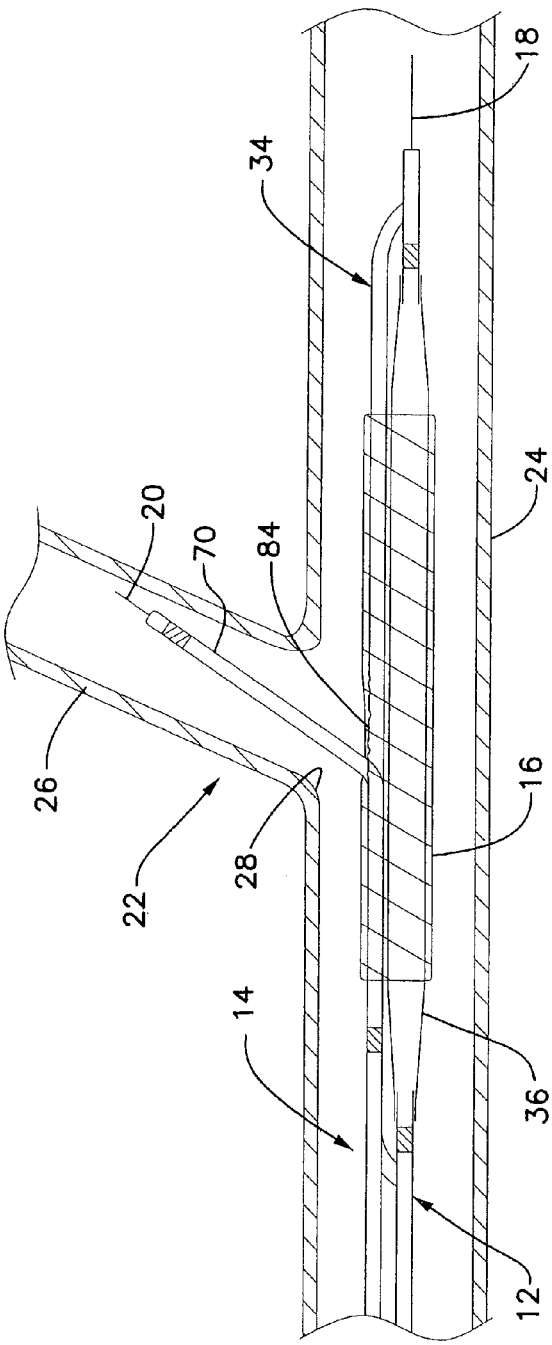

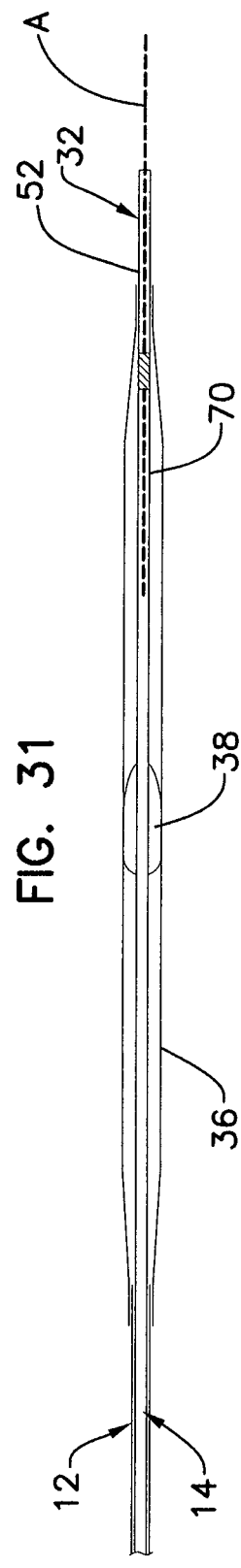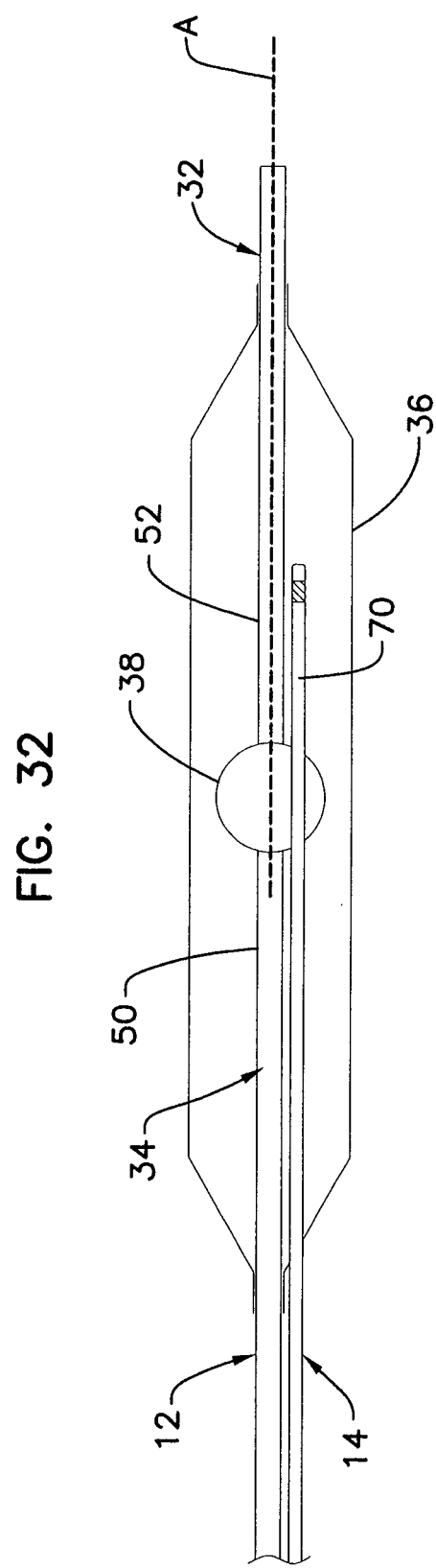

BIFURCATION CATHETER ASSEMBLY AND METHODS

RELATED APPLICATIONS

This application is a continuation of co-pending U.S. application Ser. No. 12/183,162, filed Aug. 31, 2008, the entire disclosure of which is incorporated herein by reference.

TECHNICAL FIELD

This disclosure relates to catheter systems and methods for treating vessel bifurcations. Preferred arrangements relate to inflation lumen and balloon configurations for bifurcation catheter systems.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure relates generally to catheter assemblies for treatment of bifurcated lumens in a patient, such as vessel bifurcations. In one example, a catheter assembly includes a main catheter branch and a side catheter branch. The main catheter branch includes a main balloon, a side balloon and a side inflation member. The side inflation member intersects the side balloon at a location on the side balloon that is offset laterally from a central line passing from a distal-most point on the side balloon to a proximal-most point on the side balloon. The side balloon is configured to extend radially outward relative to the main balloon when the side balloon is inflated. The side catheter branch can be centrally aligned with the side balloon central line and be positioned laterally adjacent to the side inflation lumen.

The side inflation lumen can include a proximal segment that extends proximally from the side balloon, and a distal segment that extends distally from the side balloon. Typically, at least the proximal segment intersects the side balloon laterally offset from the side balloon central line. In some arrangements, the distal segment can also intersect the side balloon at a laterally offset location from the side balloon central line.

The catheter assemblies can be used to deliver a stent to a vessel treatment site. An example stent delivered by the catheter assemblies includes a lateral branch opening through which the side catheter branch extends. The side balloon is aligned with the lateral branch opening, wherein inflation of the side balloon can help further open the lateral branch opening of the stent.

There is no requirement that an arrangement or method include all features characterized herein to obtain some advantage according to this disclosure.

BRIEF DESCRIPTION OF THE DRAWINGS

FIG. 1 is a schematic representation of an exemplary catheter assembly for treatment of a bifurcation, the assembly constructed having a proximal end portion and distal end portion, wherein the distal end portion includes main and side balloons and main and side catheter branches.

FIG. 2 is a schematic side view of the distal end portion of the catheter assembly shown in FIG. 1 with the balloons in the un-inflated state.

FIG. 3 is a schematic side view of the distal end portion of the catheter assembly shown in FIG. 1 with the balloon portions inflated and the stent expanded.

FIG. 4 is a schematic cross-sectional view taken along cross-sectional indicators 4-4 in FIG. 2.

FIG. 5 is a schematic cross-sectional view of the catheter assembly shown in FIG. 3.

FIG. 6 is a schematic top view of the catheter assembly shown in FIG. 3 with the stent removed.

FIG. 7 is a schematic is a schematic cross-sectional view taken along cross-sectional indicators 7-7 in FIG. 5.

FIG. 8 is a schematic top view of an example side balloon with an offset side inflation member segment.

FIG. 9 is a schematic top view of another example side balloon with two offset side inflation member segments.

FIG. 10 is a schematic top view of another side balloon and an alternative arrangement of two side offset inflation member segments.

FIG. 11 is a schematic rear view of an example side balloon with a side inflation member segment centrally positioned.

FIG. 12 is a schematic rear view of an example side balloon with an offset side inflation member segment.

FIG. 13 is a schematic front view of an example side balloon with an offset side inflation member segment.

FIG. 14 is a schematic top view of the side balloon and side inflation member segments shown in FIG. 8 with a centrally oriented side catheter branch.

FIG. 15 is a schematic top view of the side balloon and side inflation member arrangement shown in FIG. 9 with a centrally oriented side catheter branch.

FIG. 16 is a schematic top view of the side balloon and side inflation member arrangement shown in FIG. 10 with a centrally located side catheter branch.

FIG. 17 is a schematic rear view of the side balloon and side inflation member shown in FIG. 28 with an offset side catheter branch.

FIG. 18 is a schematic rear view of the side balloon and side inflation member arrangement shown in FIG. 15 with a centrally located side catheter branch.

FIG. 19 is a schematic front view of the side balloon and side inflation member arrangement shown in FIG. 15 with a centrally located side catheter branch.

FIG. 20 is a schematic cross-sectional side view of an example two-piece mold used to generate a side balloon from a side inflation member.

FIG. 21 is a schematic cross-sectional top view of the mold shown in FIG. 20.

FIGS. 24-26 illustrate the catheter assembly shown in FIGS. 1-7 in use treating a vessel bifurcation.

FIG. 31 is a schematic top view of the catheter assembly shown in FIG. 27 with the stent removed.

FIG. 32 is a schematic top view of the catheter assembly shown in FIG. 28 with the stent removed.

DETAILED DESCRIPTION

Figure 22:
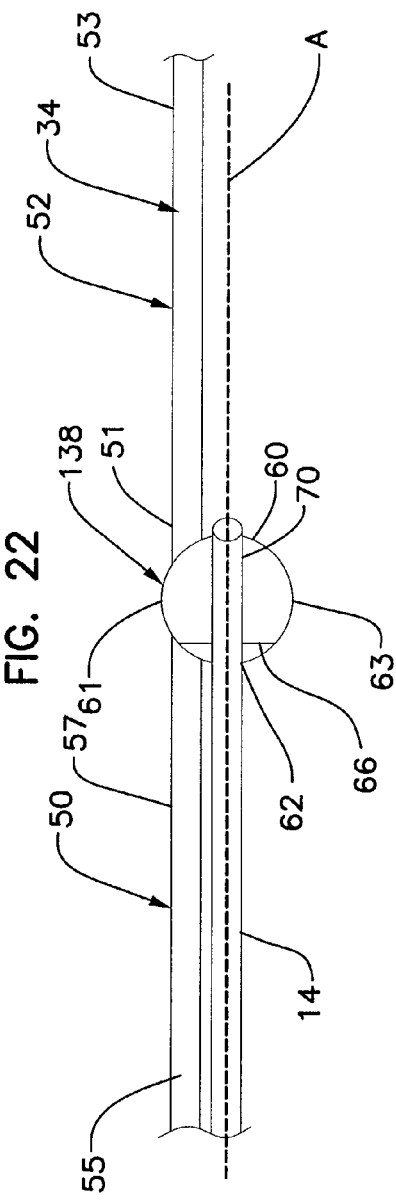
FIG. 22 is a schematic top view of an example side balloon with offset side inflation member segments and a centrally oriented side catheter branch, wherein the side balloon includes an angled surface.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein to can be used for locating a branch vessel of the vessel bifurcation and for placement of a stent relative to the vessel bifurcation for treatment of the vessel bifurcation.

While alternatives are possible, the example catheter assemblies disclosed herein generally include at a distal end portion thereof a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

The main catheter branch includes a catheter shaft having a distal end portion. A main balloon and a side balloon are positioned at the distal end portion of the catheter shaft. A main catheter branch includes a main guidewire housing that defines a main guidewire lumen. The main guidewire housing extends through the main balloon. The side balloon is positioned on a side inflation member. The side inflation member can extend in parallel with a longitudinal dimension of the main balloon. The side inflation member defines a side inflation lumen. The side inflation member can include proximal and distal segments that are connected in fluid communication with the side balloon. One aspect of the present disclosure relates to the intersection point between the side inflation member and the side balloon. The side inflation member can intersect the side balloon at a location that is laterally offset from a central proximal-distal line of the side balloon. The central proximal-distal line of the side balloon extends from a proximal-most point on the side balloon to a distal-most point on the side balloon. Typically, the central proximal-distal line of the side balloon is also located centrally between opposing laterally offset sides of the side balloon (e.g., sides 61-63 in FIGS. 8-10). The location of the central proximal-distal line can also be defined as the line that divides the side balloon in half in a projection view of the side balloon, wherein the projection view is that view from a direction in which the side balloon extends radially outward from the main balloon (e.g., see FIGS. 8-10).

Another aspect of the present disclosure relates to various configurations of the side balloon (e.g., shape and size) and the interface between the side balloon and the side catheter branch when the side balloon is inflated.

Referring now to FIGS. 27-31, an example catheter assembly 200 is shown and described. The catheter assembly 200 includes a main catheter branch 12, a side catheter branch 14, and a stent 16. The main catheter branch 12 includes a catheter shaft 30 having a distal end portion 42, a guidewire housing 32, a main balloon 36, a side inflation member 34, and a side balloon 38. The side catheter branch 14 has a distal end portion 70. The stent 16 is operably mounted to the main balloon 36, side inflation member 34, and the side catheter branch 14 using, for example, crimping techniques. The distal end portion 70 of the side catheter branch 14 extends into the stent 16 through a proximal end 82 thereof, and protrudes out of a lateral branch opening 84. The lateral branch opening is positioned on the stent at a location between the proximal and distal open ends 82, 80.

Figure 29:
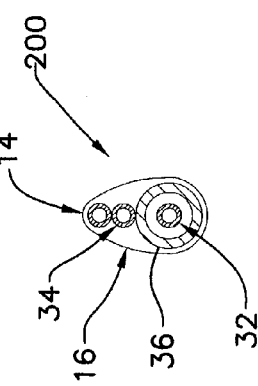
FIG. 29 is a schematic cross-sectional view taken along cross-sectional indicators 29-29 in FIG. 27.

The catheter assembly has a first distal profile P1 at a location distal the lateral branch opening 84, and a second distal profile P2 at a location proximal of the lateral branch opening 84 and distal of the proximal end 82 of the stent. As shown in FIG. 29, the profile P2 results from stacking the proximal segment of the side inflation member on top of the main balloon, and stacking the side catheter branch 14 on top of the side inflation member 34. Such stacking of the side inflation member 34 and the side catheter branch 14 helps maintain the side catheter branch 14 centrally aligned with a central proximal-distal line A of the side balloon 38 (see FIG. 32). The profiles P1, P2 can generally be the same, wherein a difference between P1 and P2 being that the side catheter branch is positioned outside of the stent for the profile P1 versus inside the stent for the profile P2. In one example, the profiles P1, P2 are each in the range of about 0.055 in. to about 0.062 in., inclusive.

Figure 30:
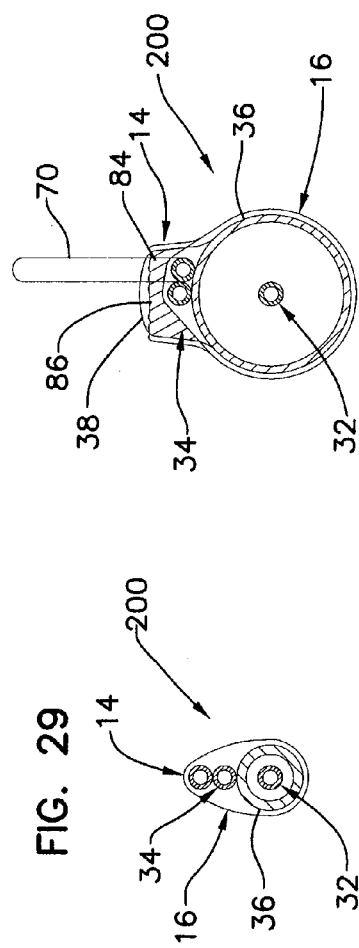
FIG. 30 is a schematic cross-sectional view taken along cross-sectional indicators 30-30 in FIG. 28.

When the main and branch balloons 36, 38 are inflated, the side catheter branch 14 typically moves laterally into a position from on top of the proximal segment of the side inflation member to a position laterally adjacent to the proximal segment of the side inflation member 34 as shown in FIG. 30. This lateral shifting of the side catheter branch results in the side catheter branch not being aligned centrally with the central proximal-distal line A of the side balloon 38 as shown in FIG. 32. FIG. 31 illustrates how the side catheter branch 14 is aligned with the side inflation member 34 and side balloon 36 along the central proximal-distal line A prior to inflation of the main and side balloons 36, 38. FIG. 32 illustrates how the side catheter branch 14 is shifted laterally (laterally to the right in this arrangement) relative to the central proximal-distal line A of the side balloon 38.

When the side catheter branch 14 shifts laterally in this manner, the side catheter branch 14 typically is offset from being centrally aligned with the lateral branch opening 84 of the stent 16 as shown in FIG. 30. Typically, the side catheter branch 14 shifts around to a right or left side of the side balloon 38, which results in the side catheter branch 14 extending out of the lateral branch opening 84 along the left or right side of the lateral branch opening 84. A side catheter branch that is not aligned centrally with the lateral branch opening of the stent can affect proper alignment of the lateral branch opening 86 with an opening into a branch vessel of a vessel bifurcation as will be discussed in further detail below with reference to FIGS. 24-26.

Referring now to FIG. 11, an example side balloon 38 is shown from a rear or proximal view. The proximal segment of the side inflation member 34 is positioned at a center location at a portion across the width of the side balloon 38 along the proximal side 62. When the side balloon 38 and side inflation lumen 34 are used with a side catheter branch 14 as described above with reference to FIGS. 27-32, the side catheter branch 14 tends to shift laterally as shown in FIG. 17 so as to be positioned laterally adjacent to the proximal segment 50 of the side inflation member 34 at a location proximal of the side balloon 38. FIG. 17 illustrates the side catheter branch 14 positioned to the right of the side inflation member 34 such that the distal end portion 70 of the side catheter branch 14 extends along the right side 63 and across the radially outward facing surface 64 of the side balloon 38 when the side balloon 38 is inflated. In other instances, the side catheter branch 14 shifts laterally to the left so as to be aligned along the left side 61 of the side balloon 38.

Other example catheter assemblies disclosed herein with reference to FIGS. 1-26 include various configurations for attachment of the side inflation member distal and proximal segments to the side balloon. These arrangements can improve alignment of the side catheter branch 14 centrally with the central proximal-distal line of the side balloon when the side and main balloons are inflated. By maintaining proper orientation of the side catheter branch relative to the side balloon, the catheter assemblies disclosed herein can provide improved consistency in aligning the lateral branch opening of the stent with the ostium of the branch vessel when treating a vessel bifurcation.

An example catheter assembly 10 is shown schematically with reference to FIGS. 1-7. The catheter assembly 10 is configured for treatment of a vessel bifurcation such as the vessel bifurcation 22 shown in FIGS. 24-26. While alternatives are possible, the catheter assembly 10 generally includes a main catheter branch 12, a side catheter branch 14, and a stent 16. The main catheter branch 12 includes a catheter shaft 30 having a proximal end portion 40 (see FIG. 1) and a distal end portion 42. The catheter shaft 30 defines an inflation lumen 44 (see FIG. 7) that extends from the proximal end portion 40 to the distal end portion 42.

The main catheter branch 12 further includes a main guidewire housing 32 having a distal end portion 48. The main guidewire housing 32 defines a main guidewire lumen 46 as shown in FIG. 7 that is sized to advance over a main guidewire. The main guidewire housing 32 can extend within the catheter shaft 30 between the proximal and distal end portions 40, 42. Alternatively, the main guidewire housing 32 can be configured as a rapid exchange arrangement wherein the main guidewire housing extends along only a portion of the length of the catheter shaft 30.

The main catheter branch can also include a main balloon 36 extending along the distal end portion 48 of the guidewire housing 32. A proximal end of the main balloon 36 extends from the proximal end portion of the catheter shaft 30, and a distal end of the main balloon 36 is secured to the main guidewire housing 32 at the distal end portion 48 (see FIG. 7).

The main catheter branch 12 further includes a side inflation member 34. The side inflation member 34 includes a proximal segment 50 having proximal and distal ends 51, 53, and a distal segment 52 having proximal and distal ends 55, 57 (see FIG. 7). The side inflation member defines a side inflation lumen 54 through which inflation fluid is provided to a side balloon 38. The side balloon includes distal and proximal sides 60, 62, left and right sides 61, 63 (also referred to as opposing laterally offset sides), and a radially outward facing surface 64. When un-inflated, the side balloon 38 maintains a generally collapsed profile (e.g., see side balloon 38 in the collapsed state shown in FIGS. 27 and 31). When inflated, the side balloon extends radially outward relative to the side inflation member 34 and the main balloon 36 (see FIGS. 3, 5 and 7). The side balloon 38 typically has a width W (see FIG. 6), a length L (see FIG. 6), and height H (see FIG. 7). The side balloon 38 illustrated in FIGS. 1-26 has a generally cylindrical shape with a circular cross-section. In other examples, the side balloon can have a variety of different shapes, sizes and cross-sections.

The side balloon can extend from the side inflation member 34 and the main balloon 36 (i.e. a longitudinal axis or a longitudinal dimension of the side balloon and main balloon (e.g. axis B shown in FIG. 3)) at an angle different from the generally 90° (perpendicular) angle shown in the Figures. While alternatives are possible, the side balloon 38 can generally extend from the side inflation member 34 and the main balloon 36 at an angle in the range of about 30° to about 90°, inclusive.

FIGS. 1 and 2 illustrate the catheter assembly 10 with the main and side balloons 36, 38 in an un-inflated state. FIG. 4 illustrates the catheter assembly 10 with the main and branch balloons 36, 38 in an inflated state. FIG. 4 illustrates the relative arrangement of the side inflation member 34, side catheter branch 14, and main balloon 36 proximal of the lateral branch opening 84 in the stent 16. The side inflation member 34 and side catheter branch 14 are positioned laterally adjacent to each other and resting in contact with an outer surface of the balloon 36.

In the inflated state shown in FIGS. 3, 5, 6 and 7, the side inflation member 34 is positioned offset laterally to the left relative to the central proximal-distal line A of the side balloon 38. The side inflation member 34 can also be offset from a central plane C (see FIG. 5) that extends through the central proximal-distal line A and a longitudinal axis B of the main balloon 36 (see FIG. 3). The offset orientation of the side inflation member 34 provides space for the side catheter branch 14 to remain aligned with the central proximal-distal line A of the side balloon 38 as well as being centrally oriented relative to the lateral branch opening 84 of the stent 16.

FIG. 6 illustrates a particular arrangement for connection of the proximal and distal segments 50, 52 of the side inflation member 34 to the proximal and distal sides 62, 60 of the side balloon 38, respectively. The distal end 53 of the proximal segment 50 is connected to the proximal side 62 of the side balloon at a position offset towards the left side 61 of the side balloon. The proximal end 55 of the distal segment 52 is connected to the side balloon 38 along the distal side 60 at an orientation offset laterally from the central proximal-distal line A to the left side 61. This laterally offset arrangement of the proximal and distal segments 50, 52 relative to the central proximal-distal line A of the side balloon 38 permits orientation of the side catheter branch 14 along the central proximal-distal line A before and after inflation of the main and side balloons 36, 38. This arrangement typically provides at least two possible advantages.

One possible advantage of intersecting the side inflation member 34 with the side balloon 38 at a location laterally offset from the central proximal-distal line A is that the profiles P3, P4 of the catheter assembly 10 in the un-inflated state shown in FIG. 2 can be reduced as compared to an arrangement wherein the side catheter branch 14 is stacked on top of the side inflation member 34. Typically, the profiles P3, P4 (representing the maximum outer dimension of the catheter assembly along the stent 16 at locations distal and proximal of the lateral branch opening 84, respectively), are each less than the profiles P1, P2 of the catheter assembly 200 described above. This reduced profile results from the ability to position the side catheter branch 14 laterally adjacent to the side inflation member 34 in the catheter assembly 10 instead of vertically on top of the side inflation member 34 (see catheter assembly 200 in FIGS. 27-30).

Another possible advantage of intersecting the side inflation member 34 with the side balloon 38 at a location laterally offset from the central proximal-distal line A relates to maintaining alignment of the side catheter branch 14 along the central proximal-distal line A of the side balloon 38 before, during and after inflation of the main and side balloons 36, 38.

FIGS. 8-10 illustrate several connection arrangements of the distal and proximal segments of the side inflation member 34 to a side balloon 38. FIGS. 14-16 illustrate the arrangements of FIGS. 8-10 in combination with a side catheter branch 14 arranged along a central proximal-distal line A of the side balloon 38. FIGS. 8 and 14 illustrate intersection of the proximal segment 50 at its distal end 53 with the proximal side 62 of the side balloon at a location offset laterally towards the right side 63 of the side balloon. The distal segment 52 intersects at its proximal end 55 with the distal side 60 of the side balloon and is aligned along the central proximal-distal line A of the side balloon 38.

FIGS. 9 and 15 illustrate the proximal segment 50 intersects at the proximal side 62 offset towards the right side 63 of the side balloon. The distal segment 52 intersects at the distal side 60 of the side balloon offset to the left side 61 of the balloon. FIGS. 10 and 16 illustrate the proximal and distal segments 50, 52 intersect with the proximal and distal sides 62, 60 of the side balloon and laterally offset towards the right side 63 of the side balloon 38.

The arrangement of FIGS. 8 and 14 can be modified in other examples to offset the proximal segment 50 to the left side 61 rather than towards the right side 63 as shown. Likewise, in FIGS. 9 and 15 the proximal segment 50 can be offset towards the left side 61 and the distal segment 52 can be offset towards the right side 63 in other examples. The mirror image of the arrangement in FIGS. 10 and 16 is illustrated in FIG. 6.

FIGS. 12 and 13 illustrate the distal and proximal sides 60, 62 of the side balloon 38 and the various intersection points of the proximal and distal segments 50, 52 at offset locations to the left or right sides 61, 63 of the side balloon 38. FIGS. 18 and 19 illustrate the arrangements of FIGS. 12 and 13 and further illustrate positioning of the side catheter branch 14 centrally relative to the side balloon 38 between the left and right sides 61, 63. In one example, the maximum width dimension of the proximal and distal segments 50, 52 of the side inflation member 34 is substantially the same as the maximum width dimension of the side catheter branch 14 in the area of the side balloon 38. Therefore, offsetting the segments 50, 52 to either the left or right side relative to a position of the segments 50, 52 aligned with the central proximal-distal line A a distance equal to half of that maximum width dimension will permit orientation of the side catheter branch 14 along the central proximal-distal line A.

The maximum width W of the balloon 38 (see FIGS. 12 and 18) in one example can be about three times the maximum width dimension of the side catheter branch 14 or the side inflation member 34. With these dimensions for the side balloon 38, the side catheter branch 14 can remain centrally aligned with the central proximal-distal line A and the segments of the side inflation member 34 can be positioned on either the left or the right side of the side catheter branch 14 without the side inflation member 38 protruding laterally beyond the width of the side balloon 38. In some preferred arrangements, the side inflation member 34 does not extend laterally beyond the left or right side 61, 63 beyond the width W of the side balloon 38. In other examples, the side balloon can have any width W or other dimension that is unrelated to the maximum width dimensions of either the side catheter branch 14 or the side inflation member 34.

Referring again to FIGS. 9 and 15, the intersection of the proximal and distal segments 50, 52 at laterally offset orientations to the right or left (or vice versa) of the central proximal-distal line A of side balloon 38 can provide additional advantages when inflating the main and branch balloons 36, 38. The catheter assembly 10 shown in FIGS. 1-7 includes a side inflation member 34 that is connected at its proximal-most and distal-most ends to the catheter shaft 30 and main guidewire housing 32, respectively (i.e., at the distal end of the distal segment 52 and the proximal end of the proximal segment 50). Typically, the length of the side inflation member 34 between these proximal and distal connection points is such that prior to inflation of the main and side balloons 36, 34, there is relatively little slack or extra length in the side inflation member 34. While additional advantages are possible, minimizing the length of the side inflation member between the proximal and distal connection points can help, for example, minimize the profiles P3, P4, improve alignment of the lateral branch opening with the side balloon during assembly of the catheter assembly 10 (e.g., crimping the stent 16 in place on the main balloon 36 with the side balloon 38 aligned with the lateral branch opening 34), and reduce the incidence of loose material and structure at the distal end portion of the catheter assembly to improve ease of advancing the catheter assembly 10 to a bifurcation treatment site.

Providing the side inflation member 34 with a minimum length between the proximal-most and distal-most connection points can result in additional tension forces in the side inflation member generated when inflating the main balloon 36. Inflation of the main balloon 36 increases the length of the path that the side inflation member 34 must traverse between the proximal-most and distal-most connection points. These additional tension forces in the side inflation member can be problematic. For example, the additional tension forces can weaken the connection between the side inflation member segments 50, 52 and the side balloon 38, weaken the connection point at the proximal-most and distal-most connection points of the side inflation member 34 to the main guidewire housing 32 at a point distal of the main balloon 36 and the catheter shaft 30 at a point proximal of the main balloon 36, create deformations in the main balloon 38 outer profile, or create some misalignment between the side balloon 38 and the lateral branch opening 84 of the stent 16.

Referring again to FIGS. 9 and 15, laterally offsetting the proximal and distal segments 50, 52 in opposing directions relative to the central proximal-distal line A of the side balloon 38 can result in a rotational force that rotate the side balloon 38 when the main balloon 36 is inflated and tension is generated along the length of the side inflation member 34. This rotational force can slightly lengthen the side inflation member or at least provide some flexibility in the side inflation member 34 that can minimize the generation of the potential tension induced concerns discussed above. The rotation effect can be further magnified if the intersection point between the distal end 57 of the proximal segment is along the side 63 further around towards the distal side 60 of the side balloon. Likewise, intersecting the proximal end 51 of the distal segment 52 with the balloon at a location further along the side 61 of the balloon around towards the proximal side 62 of the balloon can create further rotation of the side balloon 38 and flexibility during inflation of the main and side balloons 36, 38 that can be advantageous.

FIGS. 20 and 21 illustrate an example mold used in creating a side balloon 38 from the side inflation member 34. The mold 90 includes a proximal portion 92 and a distal portion 94 that together define a balloon cavity 96, a proximal segment cavity 98, and a distal segment cavity 100. The mold 90 can be configured such that the balloon cavity defines any desired balloon shape, size and orientation relative to the inflation member 34. The arrangement of the proximal and distal segment cavities 98, 100 relative to the balloon cavity 96 results in a desired laterally offset intersection of one or more of the proximal and distal segments 50, 52 of the side inflation member with the side balloon 38.

In operation, a side inflation member 38 is positioned within the cavities 96, 98, 100. Heat is applied to the mold 90 and pressure is applied internal the side inflation member 34 that results in expansion of portions of the side inflation member 34 to fill the balloon cavity 96. Typically, the mold is heated using an external source of heat such as hot water or hot air. Pressure is applied internally in the side inflation member 34 by filling the side inflation member 34 with a fluid such as heated water. The resulting wall thickness of the side balloon 38 can be modified by, in addition to changing the size of the balloon cavity 96, increasing or reducing the thickness of portions of the side inflation member 34 prior to the molding process. The thickness of the side inflation member 34 can also be reduced after the molding process to reduce the wall thickness of the balloon 38 (e.g., using grinding or other material removal techniques).

The two-part design of the mold 90 is advantageous for removing the molded product from the mold 90 since the side balloon 38 is now molded integral with the side inflation member 34 and would be difficult to remove otherwise. The mold 90 shape and two-piece configuration is exemplary only. Other configurations, such as molds having three or more pieces are possible in other examples.

Figure 23:
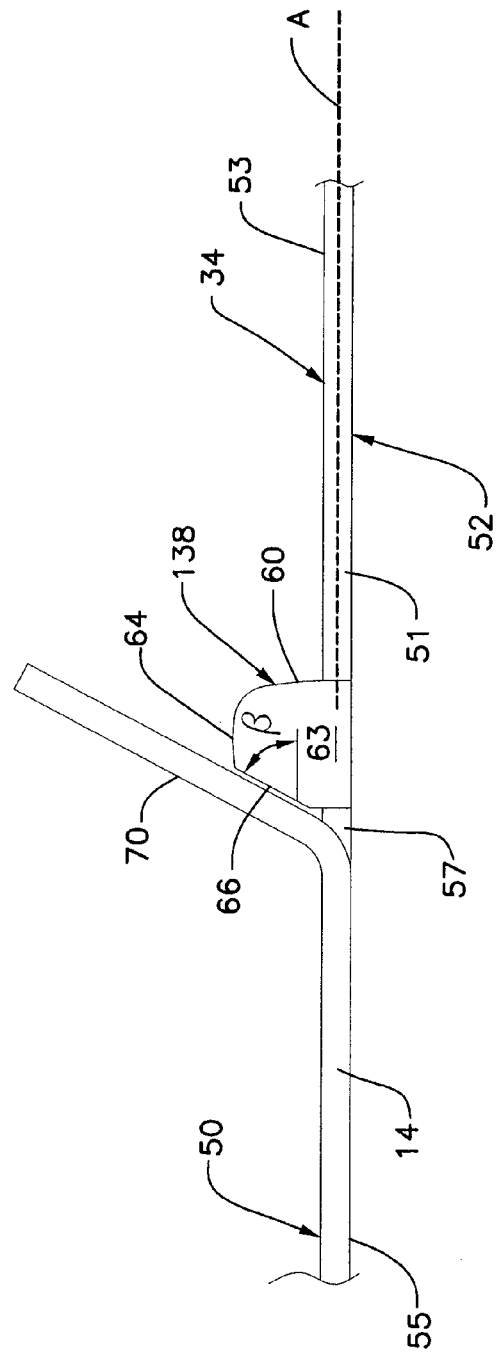
FIG. 23 is a schematic side view of the side balloon, side inflation member, and side catheter branch shown in FIG. 22.

FIGS. 22 and 23 illustrate a side balloon design that can help maintain the side catheter branch 14 in a position oriented along the central proximal-distal line A of the side balloon 38 during treatment of a vessel bifurcation. The side balloon 138 includes an angled surface 66 that extends from the proximal side 62 to the radially outward facing surface 64. The angled surface 66 is generally planar in this arrangement but can have other shapes and sizes in other arrangements. For example, the angled surface 66 can include a contoured shape portion such as a concave shaped portion. The angled surface 66 extends generally at an angle $\beta$ relative to a plane extending parallel with the central proximal-distal line A. Although alternatives are possible, the angle $\beta$ is typically an acute angle (less than 90°) facing in a distal direction. The angle $\beta$ is typically in the range of about 15° to about 90°, and preferably in the range of about 30° to about 75°.

The orientation of angled surface 66 relative to the side balloon 38 can be altered depending on the orientation of the side balloon 38 relative to the side inflation member 34 and the main balloon 36. For example, if the side balloon 38 extends radially away from the side inflation member 34 and main balloon 36 at an angle less than 90° (e.g., in the range of about 30° to about (80°), the angle may be smaller while still providing the desired function.

The angled surface 66 can have advantages related to keeping the side catheter branch 14 from moving laterally as the side balloon and main balloon 38,36 inflate. Typically, the side balloon 38 can include a generally cylindrical, spherical, hemispherical shape with many different cross-sectional shapes possible. The side balloon 38 can also typically includes a rounded or convex shaped outward facing surface 64. Since many surfaces of such side balloon constructions are contoured in a convex direction, contact between the side catheter branch 14 and the side balloon 38 is usually a point (assuming no concave deformation of the side catheter branch 14 and side balloon 38). This type of minimum contact on a convex surface can make it more difficult to maintain a single position of the side catheter branch aligned along the central proximal-distal line A of the side balloon 38. Including the generally planar angled surface 66 along the proximal side 62 provides a more substantial contact surface between the side catheter branch 14 and the side balloon 38. Further, lack of curvature across the width of the surface 66 can make it easier to maintain alignment of the side catheter branch 14 along the central proximal-distal line A.

The addition of other structure such as convex portions, protrusions, or multiple planar surfaces in addition to or in place of the angled surface 66 can provide the same or similar effect of helping maintain alignment of the side catheter branch 14 with the central proximal-distal line A.

Figure 26:
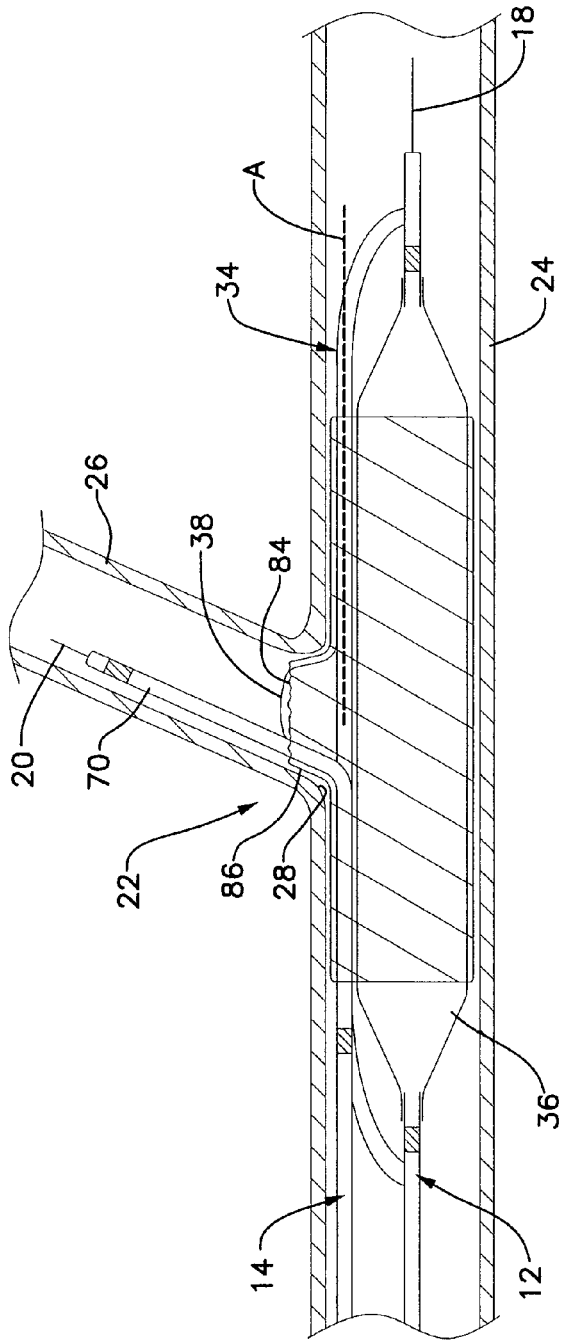
Figure 27:
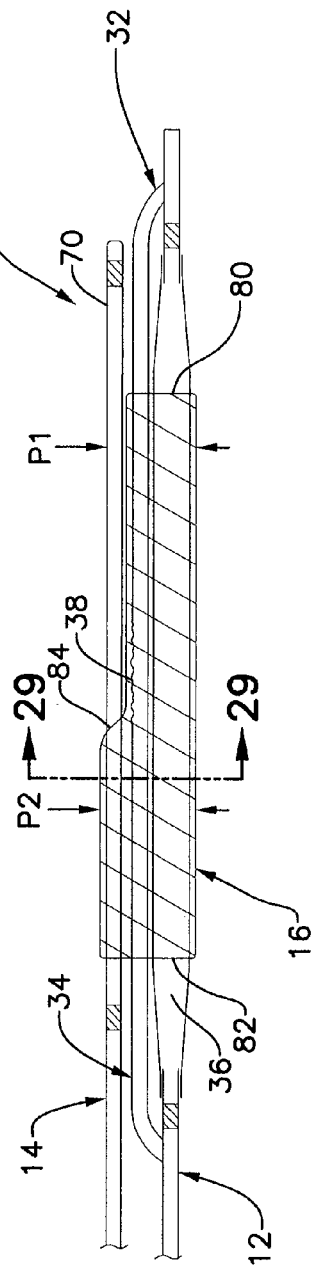
FIG. 27 illustrates the catheter assembly having a proximal side inflation member segment that is centrally located on a rear side of the side balloon.
Figure 28:
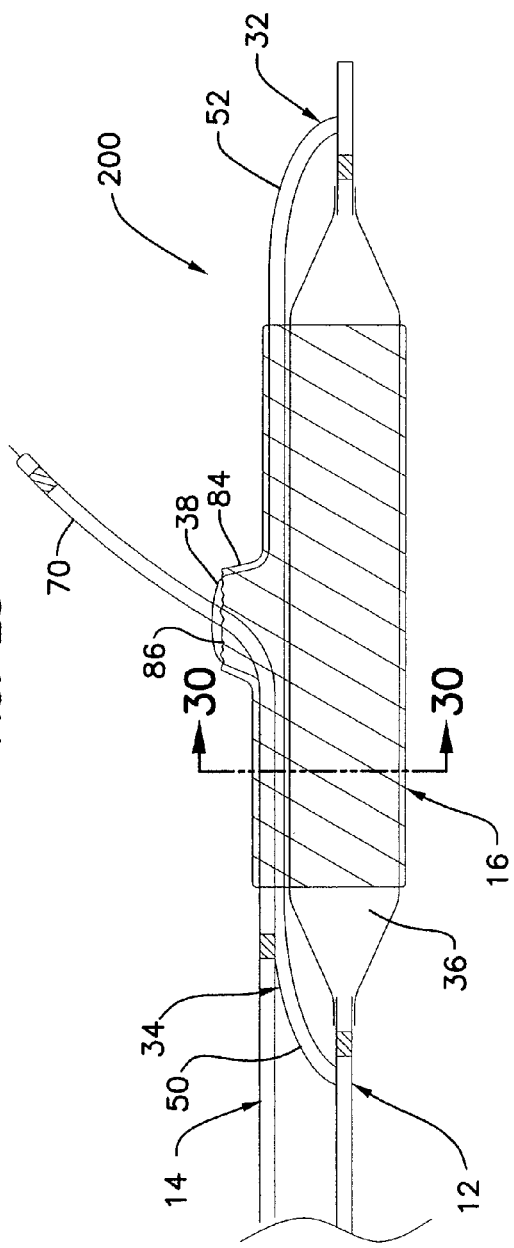
FIG. 28 illustrates the catheter assembly shown in FIG. 27 with the main and side balloons inflated.

The catheter assembly 10 described above with reference to FIGS. 1-7 can be used for treatment of a vessel bifurcation 22 as shown in FIGS. 24-26. Typically, a main vessel guidewire 18 is first inserted into a main vessel 24 of the vessel bifurcation 22 to a point distal of the vessel bifurcation. A branch vessel guidewire 20 is advanced to the vessel bifurcation and inserted through an ostium or opening 28 of a branch vessel 26. Proximal ends of the guidewires 18, 22 are then inserted into the main guidewire lumen 46 and branch guidewire lumen 72, respectively. The catheter assembly 10 is advanced over the guidewires 18, 22 to the vessel bifurcation as shown in FIG. 24. The catheter assembly 10 is advanced further distally until the distal end portion 70 of the side catheter branch 14 is positioned within the branch vessel 26. A marker system can be used to help confirm proper rotational (radial) and axial alignment of the lateral branch opening 84 of the stent 16 relative to the ostium 28 into the branch vessel 26. An example marker system is described below.

After proper axial and rotational positioning of the catheter assembly 10 is confirmed, the main and branch balloons 36, 38 are inflated. The laterally offset orientation of at least the proximal segment 50 of the side inflation member 34 provides for positioning of the side catheter branch 14 aligned with the central proximal-distal line A of the side balloon 38 prior to and during inflation of the balloons 36, 38. Central alignment of the side catheter branch 14 with the side balloon 38 can improve consistency in aligning the lateral branch opening 84 with the ostium 28 of the vessel bifurcation. Typically, inflation of the side balloon 38 can also result in expansion of expandable structure 86 surrounding the lateral branch opening 84. The expanded expandable structure 86 can extend through the ostium 28 and at least partially into the branch vessel 26.

In a follow-up step, after the balloons 36, 38 have been deflated and the catheter branches 12, 14 retracted proximally, a separate balloon member (not shown) can be advanced through the lateral branch opening to treat the branch vessel 26 and further open the expandable structure 86 into the branch vessel 26. In a still further step, an additional branch stent can be advanced through the lateral branch opening 84 and into the branch vessel and expanded to treat further the branch vessel 26.

The particular method steps described above can be altered in other example treatment methods. For example, one of the guidewires 18, 20 can be advanced with the catheter assembly 10 to the vessel bifurcation. In another example, the balloons 36, 38 can be inflated sequentially rather than simultaneously for purposes of, for example, improving alignment of the lateral branch opening 84 with the ostium into the branch vessel.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429; 6,325,826; 6,706,062; and 7,220,275, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen or inner volume of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX®70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

The catheter assembly 10 can include marker material that is visible under X-ray or in fluoroscopy procedures. FIG. 2 illustrates markers 1-4 positioned along the distal end portions of the main and side catheter branches 12, 14. Any features of the system 10 that include marker material can be more easily identified and distinguished under X-ray or in fluoroscopy procedures. Some example marker materials include gold, platinum and tungsten. In one embodiment, the marker material can be included in a band structure that is secured to at least one of the main and side catheter branches 12, 14. In other embodiments, the marker material is part of the material composition of portions of the main and side catheter branches 12, 14. Viewability of features of the catheter assembly 10 under X-ray or fluoroscopy can assist the physician operating the system 10 to more easily adjust a position of the system 10 relative to the vessel bifurcation 40. Example markers and marker materials suitable for use with system 10 are described in U.S. Pat. No. 6,692,483 to Vardi, et al., and co-pending U.S. Published Patent Application No. 2007/0203562, filed on Feb. 22, 2007, and titled MARKER ARRANGEMENT FOR BIFURCATION CATHETER, which matters are incorporated herein by reference.

Alternative catheter assemblies to those described above are configured for use with stents having self-expanding features. Self-expanding stents and self-expanding features of a stent typically do not require the use of an inflatable member such as a balloon to expand the sent or stent feature. Typically, self-expanding stents, such as those stents described in U.S. Published Patent Application No. 2004/0176837, are held in a constricted state using a sheath that fits over the stent. In the constricted state, the stent is able to navigate through a body lumen to the treatment site. Once the stent and sheath are positioned at the treatment site, the sheath is retracted proximally to release the stent for expansion of the stent into a radially expanded state.

One aspect of the present disclosure relates to a catheter assembly that includes a stent, a main catheter branch, and a side catheter branch. The stent includes a proximal open end, a distal open end, and a lateral branch opening. The main catheter branch includes a proximal end portion and a distal end portion. The distal end portion includes a main balloon, a side balloon, and a side inflation lumen. The main balloon includes a proximal end portion, a distal end portion, and a longitudinal dimension extending between the proximal and distal end portions. The side balloon is arranged at a location between the proximal and distal end portions of the main balloon and in alignment with the lateral branch opening of the stent. The side balloon is configured to extend radially outward relative to the main balloon when the side balloon is inflated, and defines a central proximal-distal line. The side inflation member intersects the side balloon at a location offset laterally from the side balloon central proximal-distal line. The side catheter branch defines a branch guidewire lumen and extends through the lateral branch opening of the stent. The side catheter branch is centrally aligned with the side balloon central proximal-distal line.

Another aspect of the present disclosure relates to a catheter assembly that includes a main balloon, a side balloon, and a side inflation member. The main balloon includes a proximal end portion, a distal end portion, and a longitudinal dimension extending from the proximal end portion to the distal end portion. The side balloon is positioned at a location between the proximal and distal end portions of the main balloon and is configured to extend radially outward relative to the main balloon when the side balloon is inflated. The side balloon has a proximal-most point, a distal-most point, and a in central proximal-distal line that extends from the proximal-most point to the distal-most point of the side balloon. The side inflation member intersects the side balloon at a location offset laterally from the side balloon central proximal-distal axis.

A still further aspect of the present disclosure relates to a method of assembling a stent delivery system. The stent delivery system includes a stent, a main catheter branch, and a side catheter branch. The stent has a proximal open end, a distal open end, and a lateral branch opening. The main catheter branch includes a main balloon, a side balloon and a side inflation member, wherein the side balloon defines a central proximal-distal line, and the side inflation member intersects the side balloon at a location offset laterally from the side balloon central proximal-distal line. The side catheter branch defines a branch guidewire lumen. Steps of the method include extending the main catheter branch into the stent with the main balloon and the side balloon positioned in the stent and the side balloon aligned with the lateral branch opening of the stent, extending the side catheter branch into the stent with a portion of the side catheter branch extending through the later branch opening of the stent and the side catheter branch centrally aligned with the side balloon central proximal-distal line, and crimping the stent into releasable engagement with the main catheter branch and the side catheter branch.

It is noted that not all of the features characterized herein need to be incorporated within a given arrangement, for the arrangement to include improvements according to the present disclosure.

What we claim is:

1. A catheter assembly, comprising:
    (a) a stent having a proximal open end, a distal open end, and a lateral branch opening;
    (b) a main catheter branch having a proximal end portion and a distal end portion, the distal end portion including:
        i. a main balloon, the main balloon having a proximal end portion, a distal end portion, and a longitudinal axis extending between the proximal and distal end portions;
        ii. a side balloon arranged at a location between the proximal and distal end portions of the main balloon and in alignment with the lateral branch opening of the stent, the side balloon configured to extend radially outward relative to the main balloon when the side balloon is inflated, the side balloon defining a central proximal-distal line;
        iii. a side inflation member including proximal and distal segments that intersect the side balloon at locations offset laterally from the side balloon central proximal-distal line, wherein the proximal and distal segments are laterally offset in opposing directions relative to the central proximal-distal line; and
    (c) a side catheter branch defining a branch guidewire lumen, the side catheter branch extending through the lateral branch opening of the stent, the side catheter branch being centrally aligned with the side balloon central proximal-distal line.

2. The assembly of claim 1, wherein the proximal segment extends from the side balloon in a proximal direction on one side of the central proximal-distal line, and the distal segment extends from the side balloon in a distal direction on the opposite side of the central proximal-distal line.

3. The assembly of claim 1, wherein the main catheter branch further includes:
    (a) a catheter shaft having a distal end portion and defining a main inflation lumen; and
    (b) a main guidewire housing defining a main guidewire lumen, the main guidewire housing extending through at least a portion of the main inflation lumen and through the main balloon from the proximal end portion to the distal end portion of the main balloon.

4. The assembly of claim 1, wherein a transverse line extending through the side balloon perpendicular to the central proximal-distal line intersects the side balloon at first and second side points, wherein the proximal segment intersects the side balloon at a location closer to the first side point than the proximal-most point, and the distal segment intersects the side balloon at a location closer to the second side point than the distal-most point.

5. The assembly of claim 1, wherein the side balloon central proximal-distal line divides the side balloon in half in a projection view of the side balloon.

6. The assembly of claim 1, wherein the proximal and distal segments are connected to the side balloon such that upon inflation of the main balloon, the side balloon rotates, thereby lengthening the side inflation member.

7. The assembly of claim 1, wherein the central proximal-distal line is parallel to the main balloon longitudinal axis.

8. A method of assembling a stent delivery system, the stent delivery system including a stent, a main catheter branch, and a side catheter branch, the stent having a proximal open end, a distal open end, and a lateral branch opening, the main catheter branch including a main balloon, a side balloon and a side inflation member, the side balloon defining a central proximal-distal line, and the side inflation member including proximal and distal segments that intersect the side balloon at locations offset laterally from the side balloon central proximal-distal line, wherein the proximal and distal segments are laterally offset in opposing directions relative to the central proximal-distal line, the side catheter branch defining a branch guidewire lumen, the method comprising:

(a) extending the main catheter branch into the stent with the main balloon and the side balloon positioned in the stent and the side balloon aligned with the lateral branch opening of the stent;

(b) extending the side catheter branch into the stent with a portion of the side catheter branch extending through the lateral branch opening of the stent and the side catheter branch centrally aligned with the side balloon central proximal-distal line; and (c) crimping the stent into releasable engagement with the main catheter branch and the side catheter branch.

9. The method of claim 8, wherein the proximal segment extends proximally from the side balloon and the distal segment extends distally from the side balloon, and extending the side catheter branch into the stent includes positioning the side catheter branch between the proximal and distal segments of the side inflation member.

10. The method of claim 8, wherein crimping the stent includes reducing an outer profile of the stent while maintaining the side balloon in alignment with the lateral branch opening and while maintaining the side catheter branch centrally aligned with the side balloon central proximal-distal line.

* * * * *

UNITED STATES PATENT AND TRADEMARK OFFICE
CERTIFICATE OF CORRECTION

PATENT NO. : 8,454,674 B2  Page 1 of 1
APPLICATION NO. : 13/440447
DATED : June 4, 2013
INVENTOR(S) : Richard C. Gunderson It is certified that error appears in the above-identified patent and that said Letters Patent is hereby corrected as shown below:

In the Specification

Column 3
Line 52: after "disclosed herein", delete "to".

Column 13
Line 32: before "central proximal-distal", delete "in".

Signed and Sealed this
Twenty-seventh Day of May, 2014

Michelle K. Lee
*Deputy Director of the United States Patent and Trademark Office*